(12) United States Patent
Wuidart et al.

(10) Patent No.: US 11,364,317 B2
(45) Date of Patent: Jun. 21, 2022

(54) CARTRIDGE FOR A FRAGRANCE DISPENSING DEVICE AND FRAGRANCE DISPENSING DEVICE

(71) Applicant: ARTIRIS, Paris (FR)

(72) Inventors: Aymeric Wuidart, Paris (FR); David Lopez-Bonet, Paris (FR)

(73) Assignee: ARTIRIS, Paris (FR)

( * ) Notice: Subject to any disclaimer, the term of this patent is extended or adjusted under 35 U.S.C. 154(b) by 0 days.

(21) Appl. No.: 17/263,430

(22) PCT Filed: Jul. 26, 2019

(86) PCT No.: PCT/EP2019/070201
§ 371 (c)(1),
(2) Date: Jan. 26, 2021

(87) PCT Pub. No.: WO2020/021076
PCT Pub. Date: Jan. 30, 2020

(65) Prior Publication Data
US 2021/0290811 A1    Sep. 23, 2021

(30) Foreign Application Priority Data
Jul. 27, 2018  (FR) ..................................... 1857018

(51) Int. Cl.
*B01F 23/21*    (2022.01)
*A61L 9/12*    (2006.01)

(52) U.S. Cl.
CPC .............. *A61L 9/122* (2013.01); *A61L 9/125* (2013.01); *B01F 23/21* (2022.01); *A61L 2209/133* (2013.01)

(58) Field of Classification Search
CPC ........ B01F 3/04; B01F 3/04085; B01F 23/21; A61L 9/122
See application file for complete search history.

(56) References Cited

U.S. PATENT DOCUMENTS

| 6,783,117 B2* | 8/2004 | Wohrle | ................... | A61L 9/035 |
| | | | | 261/104 |
| 2012/0000989 A1* | 1/2012 | Bordier | ................... | A61L 9/122 |
| | | | | 239/34 |

FOREIGN PATENT DOCUMENTS

| KR | 20-0438243 | 2/2008 |
| WO | 2016/098114 | 6/2016 |
| WO | 2018/091766 | 5/2018 |

OTHER PUBLICATIONS

International Search Report for PCT/EP2019/070201 dated Jan. 3, 2020, 8 pages.

(Continued)

*Primary Examiner* — Robert A Hopkins
(74) *Attorney, Agent, or Firm* — Nixon & Vanderhye (57) ABSTRACT

A cartridge for a fragrance dispensing device includes a hollow body having an inlet and an outlet, and an accumulator for odorant composition in the hollow body. The cartridge further includes a closer for the inlet and outlet. Also disclosed is a device for dispensing fragrances, having a housing including: at least two receptacles, each removably receiving a cartridge, each receptacle including an air inlet and exhaust, connected respectively to the inlet and outlet of a cartridge and also act on the closer of a cartridge in the receptacle to move them in the open position, a generator of air flow through the receptacles between the inlet and exhaust, and a control unit controlling the air flow generator and the inlet and exhaust and ensures an independent or simultaneous dispensing of the compositions in the cartridges in variable proportions and closure of the cartridges when the apparatus is stopped.

20 Claims, 7 Drawing Sheets

(56) References Cited

OTHER PUBLICATIONS

Written Opinion of the ISA for PCT/EP2019/070201 dated Jan. 3, 2020, 11 pages.

* cited by examiner

CARTRIDGE FOR A FRAGRANCE DISPENSING DEVICE AND FRAGRANCE DISPENSING DEVICE

CROSS-REFERENCE TO RELATED APPLICATIONS

This application is the U.S. national phase of International Application No. PCT/EP2019/070201 filed Jul. 26, 2019 which designated the U.S. and claims priority to FR 1857018 filed Jul. 27, 2018, the entire contents of each of which are hereby incorporated by reference.

BACKGROUND OF THE INVENTION

Field of the Invention

The present invention relates to the technical field of fragrance dispensing devices, and more particularly the diffusers comprising fragrance or scent cartridges. The invention also relates to a cartridge for a fragrance dispensing device.

Description of the Related Art

In the above field, dry perfume diffusers are known, which comprise cartridges, removably mounted in a diffuser, adapted to release at least one fragrance.

For example, document WO2016/098114 discloses a fragrance dispensing device comprising a casing with compartments open to the atmosphere, each being intended to receive a cartridge containing a fragrance. According to this document, each cartridge is consisted of a cylindrical hollow body that contains a fragrance container and whose top and bottom faces are perforated so as to allow the passage of a flow of air in contact with the container. Each compartment is further associated with a fan adapted to pulse air into the compartment from the base thereof and hence through the cartridge that is located therein. The system then diffuses the fragrances by modulating the speed of operation of the fans according to the user instructions.

Such a system allows the diffusion of fragrances while being easy to use, but has in particular for drawback that the container of each cartridge is always in contact with ambient air, so that the fragrances are permanently diffused, even when the fan associated with the cartridge is stopped or when the device is completely stopped. It results therefrom an uncontrolled draining of the cartridge containers and the impossibility to provide an odorant composition that would not comprise the fragrance of a certain cartridge, insofar as, even with its associated fan stopped, the latter still diffuses the aromatic principles it contains.

SUMMARY OF THE INVENTION

In order to remedy this drawback, the invention relates to a cartridge, for a fragrance dispensing device, comprising a hollow body provided with an inlet and an outlet and means for accumulating at least one odorant composition, arranged in the hollow body, and characterized in that it further comprises means for shutting the inlet and outlet, which are mobile between an open position and a closed position, biased in the closed position and airtight in the closed position.

Thus, integrating means for airtight shutting the cartridge being biased in the shutting position avoids a draining or an alteration of the cartridge content when the latter is outside the apparatus. Moreover, the means for shutting offer the possibility to obtain a perfect closure of each cartridge in the diffusion device when the fragrance contained in the cartridge is not to be used. By "airtight", it is to be understood that no air leak occurs when the pressure inside the cartridge is slightly higher than the external pressure. In this context, airtight is synonymous of hermetic.

According to a feature of the invention, the means for shutting comprise two shutters, one for the inlet and the other for the outlet.

According to another feature of the invention, the cartridge comprises at least one plug, comprising:
a link element airtightly fit on the cartridge body and comprising a seat defining a passage,
a shutter, mobile in translation, adapted to translate between an open position and a closed position of the passage, and means for biasing the shutter in the closed position.

The implementation of such a plug allows simplifying the cartridge manufacturing method and, in particular, the positioning of at least one fragrance or odorant composition into the hollow body of the accumulation means. The cartridge can hence be airtightly closed by means of plugs.

According to another feature of the invention, the means for biasing the shutter comprise a spring. The use of a spring or any other elastic member makes it possible to simply bias the shutter to a closed position. This spring can be, for example, a leaf spring or a helical spring.

According to the invention, the means for shutting are not necessarily made as a mobile element by an elastic member. Thus, the means for shutting can be made as an elastically deformable membrane with at least one slot able to open for the passage an air-flow intake or exhaust tube and to close automatically when this tube is removed. When closed, the membrane is airtight.

According to another feature of the invention, the body has, at least locally, an external rotational asymmetry, so as to define a direction of introduction of the cartridge into a compartment, of complementary shape, intended to receive it. This asymmetrical shape provides a fool-proof function avoiding a bad positioning of the cartridge in the diffusion device intended to receive it.

According to another feature of the invention, the means for accumulating at least one odorant composition comprise an absorbent material. The implementation of such an absorbent material makes it possible to form a container in which the odorant composition is absorbed, which facilitates the handling of the accumulation means, in particular for the cartridge assembly. Indeed, it is then possible to prefill the accumulation means before their positioning in the cartridge.

According to another feature of the invention, the cartridge comprises an identification means suitable for an automatic reading. The implementation of such a means allows an automatic identification of each cartridge within the diffusion apparatus, which can then modify its operating mode as a function of the information read.

The invention also relates to a fragrance dispensing device with a casing comprising:
at least two compartments, each adapted to removably receive a cartridge according to the invention, each compartment comprising air-flow intake and exhaust means that are, on the one hand, intended to be connected to the inlet and the outlet, respectively, of a cartridge arranged in the casing and, on the other hand, adapted to act on the means for shutting of a cartridge located in the compartment, so as to displace them to the open position, air-flow generation means, adapted to at least generate air flows passing through the compartments between the intake and exhaust means, a control unit adapted to control the air-flow generation means and the intake and exhaust means and adapted to provide an independent, sequential or simultaneous diffusion, in variable proportions, of the odorant compositions contained in the cartridges and a closure of the cartridges when the apparatus is stopped.

The combination of the cartridges having integrated means for biasing shutters in the closed position with intake and exhaust means controlled by the control unit makes it possible to obtain a precise modulation of the mixtures obtained, insofar as, when an odorant composition of a cartridge must not be used, the full shutting of the latter makes it possible to guarantee that no emanation from the latter will disturb the current diffusion. Moreover, the hermetic closure of the cartridges when the apparatus is stopped makes it possible to guarantee that no inadvertent diffusion of the compositions contained in these latter will occur, and also to prevent an early draining of the cartridges.

Moreover, it turned out with time that the diffusion system according to the prior art does not allow producing an olfactory composition modulation that is as subtle or precise as that which could be expected by the modulation of the fan flows. The inventors have identified the permanent opening of the cartridges as one of the causes of this defect. The inventors have also identified the fragrance mixture imperfection as another cause of the imperfection of the olfactory perception of the diffusion performed by the device according to the prior art.

In order to remedy this drawback, according to a variant embodiment, the diffusion device comprises a mixing chamber that is open to the outside through a diffusion mouth and to which the exhaust means of each of the compartments are connected upstream from the diffusion mouth. The implementation of such a diffusion chamber allows a homogeneous mixing of the different olfactory compositions coming from the cartridges before their release to atmosphere, which allows a better control of the effect or the olfactory perception obtained.

According to a feature of the invention, the mixing chamber has an elongated shape along a mean fibre, the diffusion mouth being at one end of the mixing chamber and the exhaust means are connected to the mixing chamber by pipes whose mean axis forms with the mean fibre of the mixing chamber an acute angle lower than 90 degrees, converging towards the diffusion mouth. Such a direction of the connection pipes makes it possible at least to limit potential phenomena of backflow in the connection pipes and to reduce the air noises linked to the diffusion.

According to a variant of this feature, the connection pipes extend in protrusion inside the mixing chamber. This configuration makes it possible to induce turbulences in the chamber in order to optimize therein the mixture of the olfactory compositions.

Within the meaning of the invention, an air-flow generation means can be an air pulser such as a propeller or turbine fan or also a mechanical compressor such as a membrane compressor or a piston compressor. Of course, air-flow generation means can combine several systems of the same type or of different types.

Likewise, the air-flow generation means can be common to the whole compartments or, on the contrary, be individual by comprising an air-flow generation means allocated to each compartment. According to the invention, the air-flow generation means can also be only connected to the mixture chamber when the diffusion device according to the invention has one.

According to an embodiment of the invention, the air-flow generation means comprise first means connected to the intake means of the compartments. The position of the air-flow generation means upstream from the cartridge with respect to the direction of circulation of the air flow avoids any deposition of odorant composition on the air-flow generation means.

According to a variant of this embodiment, the first air-flow generation means comprise, for each compartment, an individual air pulser piloted by the control unit. The implementation of individual air pulsers makes it possible to modulate in a simple way the air flow in each compartment and hence the quantity of olfactory composition released by each compartment.

According to another feature of the invention, the air-flow generation means comprise second means directly connected to the mixture chamber.

According to a variant of this feature, the second air-flow generation means are connected to the mixing chamber upstream from the connection of the compartments exhaust means to the mixing chamber. The implementation of second air-flow generation means directly connected to the mixing chamber makes it possible to obtain at the diffusion mouth an air flow rate higher than the sum of the air flow rates coming from the compartments, which makes it possible to perform a better mixing. Moreover, the position upstream from the second air-flow generation means prevent them to be fouled up or polluted by the olfactory compositions.

According to a variant of this feature, the second air-flow generation means comprise an air pulser connected to the mixing chamber at the opposite end of the diffusion mouth.

The implementation of such an air pulser makes it possible to generate a turbulent flow favourable for the mixing of the odorant compositions in the chamber.

According to another feature of the invention, the device comprises means for reading identification means present on the cartridges and the control unit is adapted to modify the operating mode of the device as a function of the readings.

According to another feature of the invention, each compartment has an at least partly asymmetric shape intended to cooperate with a cartridge of complementary shape, so as to define a direction of introduction of said cartridge. This feature makes it possible to provide a fool-proof function and to guide a user as regards the direction of introduction of the cartridge into its compartment.

Of course, the different features, variants and embodiments of a cartridge and of a diffusion device according to the invention can be associated with each other according to various combinations insofar as they are not incompatible or exclusive to each other.

BRIEF DESCRIPTION OF THE DRAWINGS

Moreover, various other features of the invention emerge from the appended description made with reference to the drawings that illustrate a non-limitative embodiment of a cartridge and a diffusion device according to the invention.

DESCRIPTION OF THE PREFERRED EMBODIMENTS

It is to be noted that, in these figures, the structural and/or functional elements common to the different variants can have the same references.

The invention aims to allow the diffusion of fragrances resulting in particular from the mixture-on-demand of odorant compositions. For that purpose, the invention proposes the implementation of a diffusion device in which are arranged at least two, and preferably more than two, removable cartridges each containing an odorant composition. The diffusion device according to the invention is moreover adapted to control the circulation of air in the cartridges to provide a dry diffusion of the odorant compositions contained therein.

Figure 1:
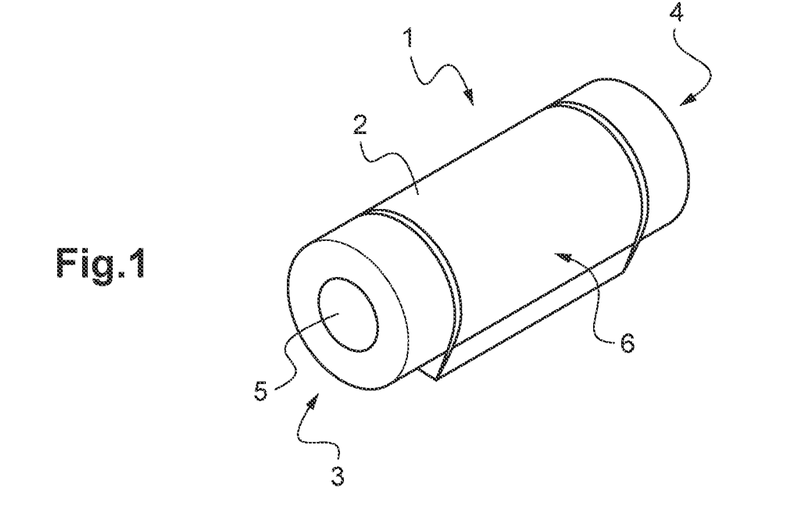
FIG. 1 is a schematic perspective view of a cartridge according to the invention.

A cartridge according to the invention, as illustrated in FIG. 1 and wholly denoted by the reference 1, comprises a hollow body 1 provided with an inlet 3 and an outlet 4, each associated with means for shutting 5 biased in the closed position, as will be understood hereinafter.

Figure 2:
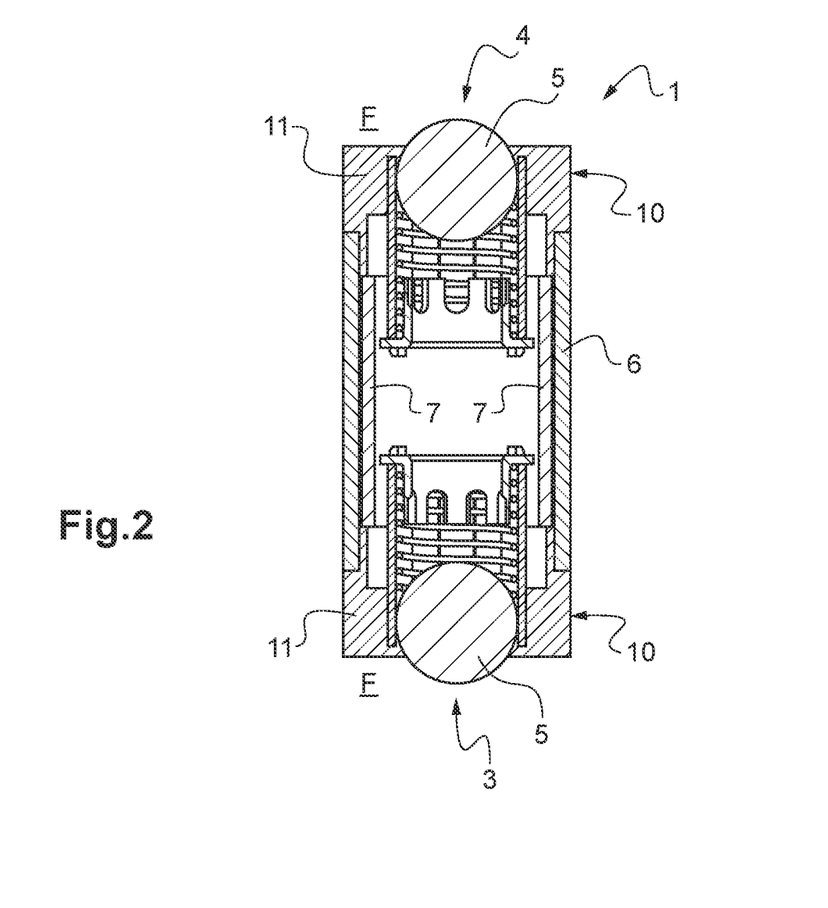
FIG. 2 is an axial cross-section of the cartridge of FIG. 1, with the means for shutting of the latter in closed position.

According to the presented embodiment and as shown in FIG. 2, the body 2 has a tubular central portion 6 of generally cylindrical shape inside which are arranged means 7 for accumulating an odorant composition. According to the illustrated example, the accumulation means are made as a skirt made of absorbent materials such as the material marketed under the brand POREX®. The accumulation means 7 then define a central channel for the circulation of an air flow in the cartridge 1. The accumulation means 7 hence form an odorant composition container adapted for a dry diffusion. The accumulation means 7 are preferably, but non necessarily, filled with an odorant composition previously to their positioning into the cartridge. As a variant, the accumulation means 7 can have other shapes, for example a rectangular shape passing through the cartridge, so as to create at least two air-flow circulation channels around this shape. Any other configuration can also be contemplated. Hence, the accumulation means can be made in the form of a set of absorbent balls randomly arranged in the cartridge.

Figure 3:
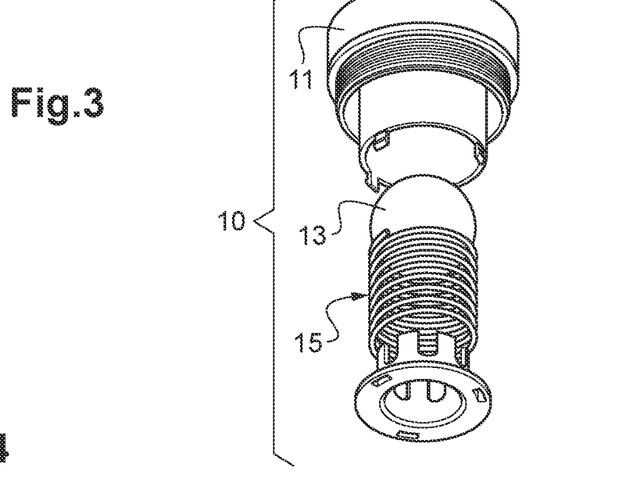
FIG. 3 is an exploded view of a plug constitutive of the cartridge of FIG. 1.
Figure 4:
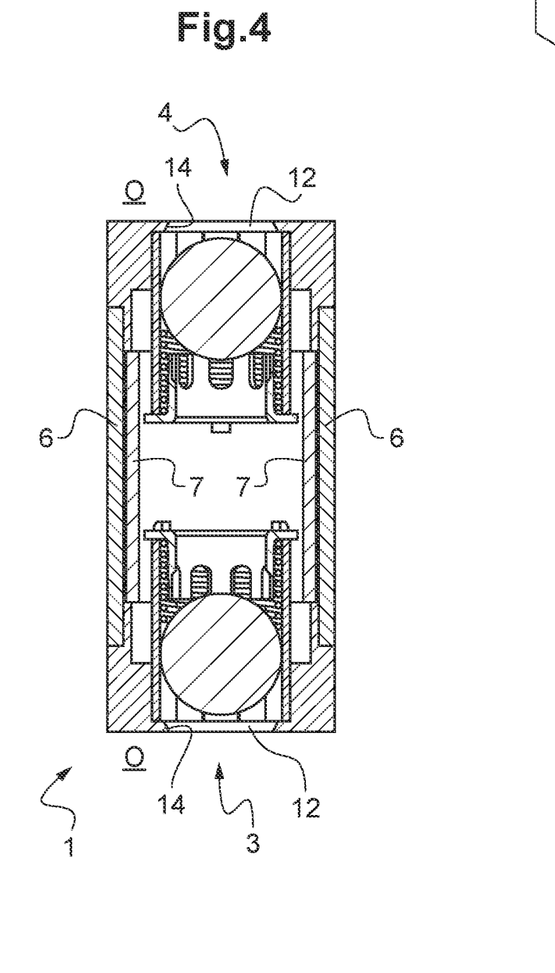
FIG. 4 is an axial cross-section similar to FIG. 2, with the cartridge means for shutting in open position.

The body 2 of the cartridge further comprises two plugs 10 that close the central portion 6 by immobilizing the accumulation means 7 inside the latter and that define the inlet 3 and the outlet 4, respectively, of the cartridge. As appear more particularly in FIG. 3, each plug 10 comprises a link element 11 airtightly fit on the central portion 6. The link element 11 further comprises a passage 12, visible in FIG. 4, forming the inlet 3 or the outlet 4 of the cartridge 1. In order to provide an airtight shutting of the passage 12, the plug 10 comprises a shutter 13 mobile in translation between a closed position F of the passage 12 and an open position O of the passage 12. In the present case, the shutter 13 is made as a ball intended to rest on a truncated seat 14 forming the passage 12. The plug 10 also comprises means for biasing 15 the shutter 13 in the closed position. In the present case, the means for biasing 15 are made in the form of a helical spring. Each plug 10 hence have a configuration that may be similar to a check valve, the two plugs being mounted in opposition on the central portion 6 of the cartridge body.

Figure 5:
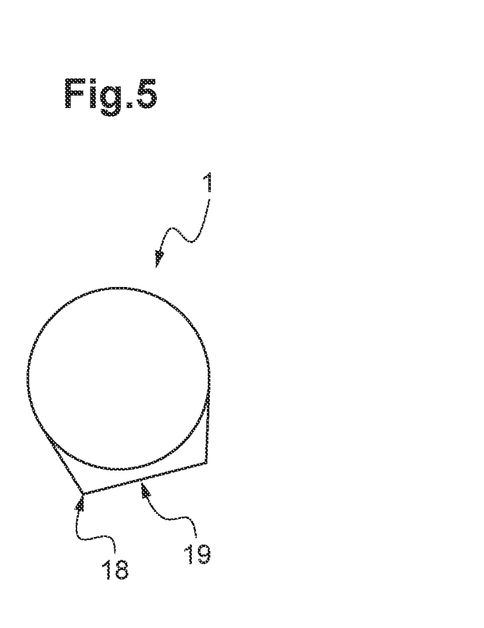
FIG. 5 is a schematic cross-section of a central portion of the cartridge illustrated in FIG. 1.

According to the illustrated example, the body 2 of the cartridge 1 has locally an external rotational asymmetry as shown in FIG. 5. In the present case, this local asymmetry is consisted of a flat 18 extending along the central portion 6 and supporting cartridge identification means 19 suitable for an automatic reading. The identification means 19 are, for example, consisted by an RFID chip.

Figure 6:
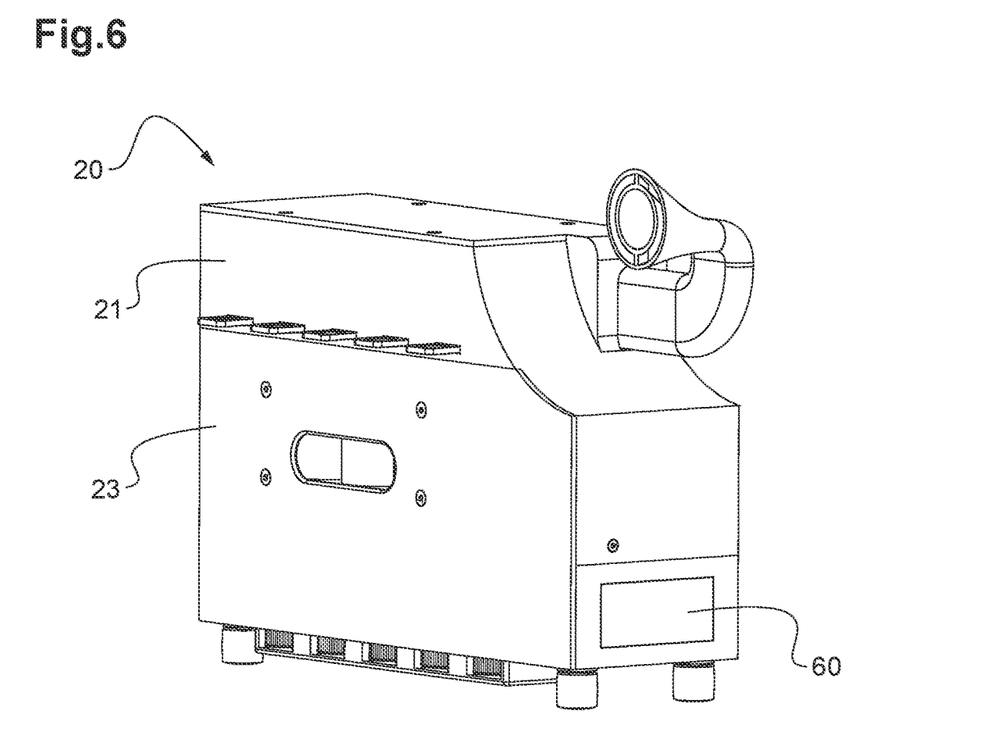
FIG. 6 is a schematic perspective view of a diffuser according to the invention.
Figure 7:
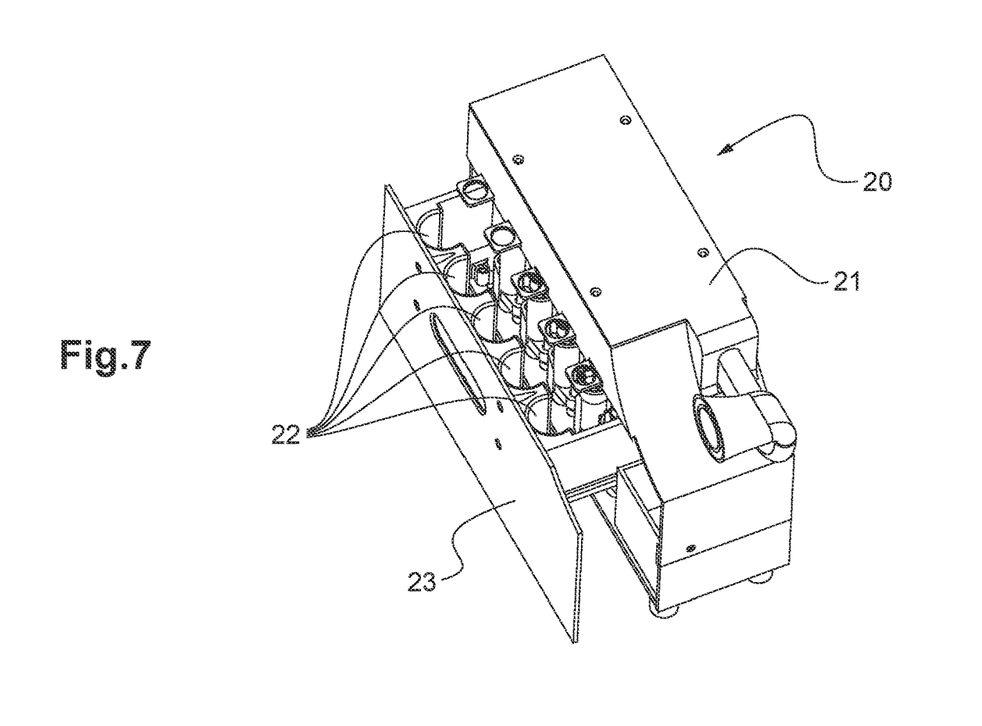
FIG. 7 is another schematic perspective view of the diffuser illustrated in FIG. 6, with an open drawer.

A so-constituted cartridge according to the invention is intended to be used in a diffusion device 20 according to the invention, as shown in FIGS. 6 and 7. According to the illustrated example, the diffusion device 20 comprises a casing 21 liable to receive five removable cartridges 1 and comprises, for that purpose, five compartments 22 arranged in a drawer 23 as shown in FIG. 7. Each compartment 22 has a shape complementary of that of the cartridge 1 and, in the present case, more particularly the central portion 6 thereof. The asymmetry of the cartridge and of the compartment of complementary shape then provides a fool-proof function guaranteeing a correct positioning of said cartridge so that the identification means 19 are arranged opposite reading means 25, visible in FIG. 8, equipping the diffusion device 20 and connected to a control unit U of the latter.

Figure 8:
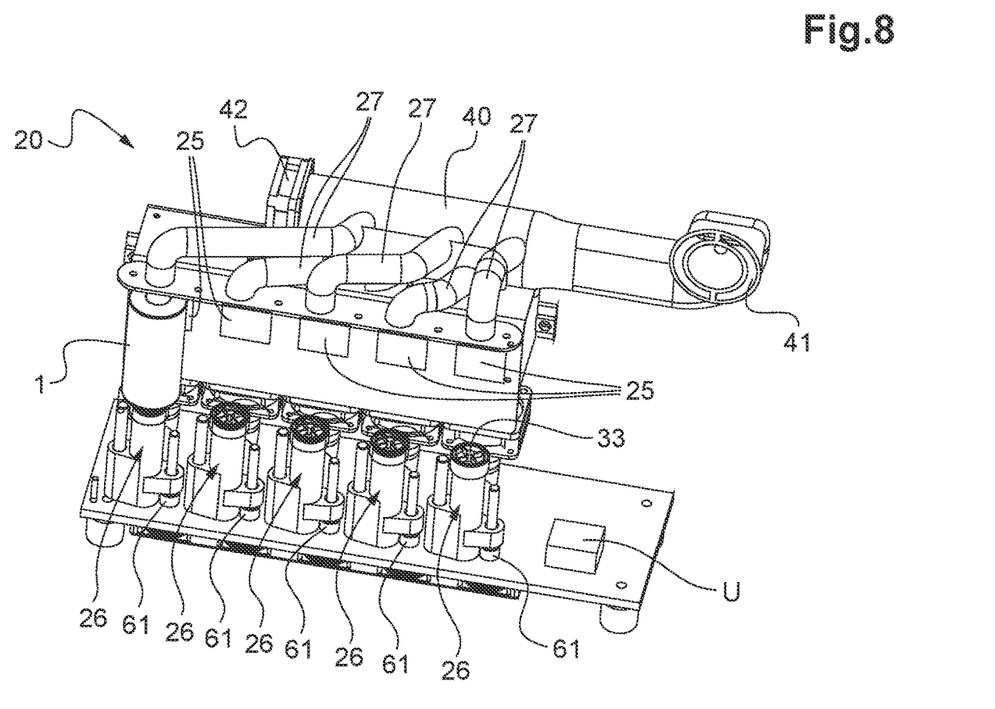
FIG. 8 is a partial, cut-away, schematic perspective view of the diffuser illustrated in FIG. 6, showing the constructive details of the latter.
Figure 9:
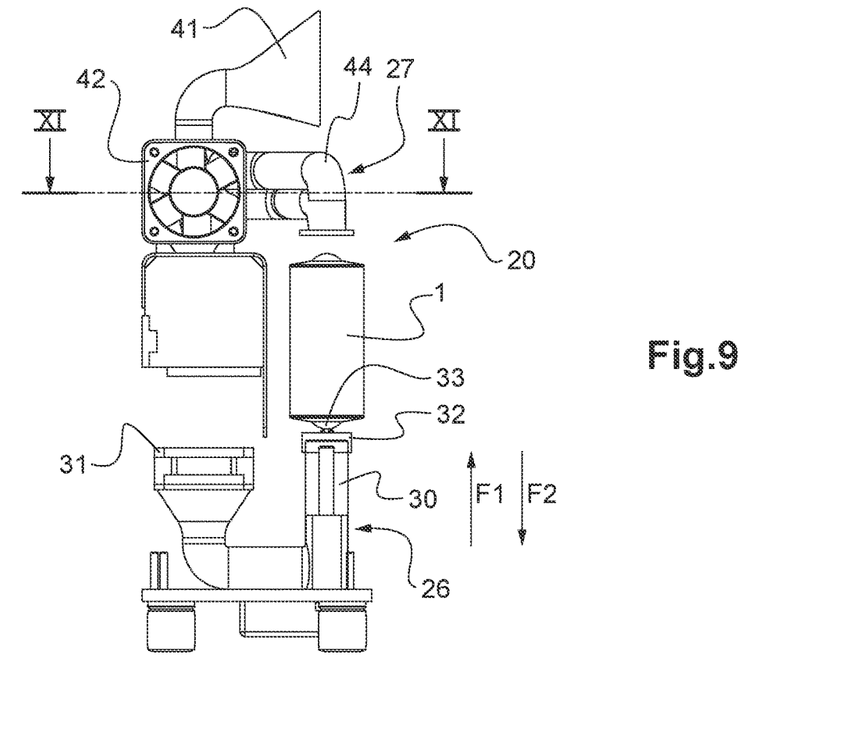
FIG. 9 is a left view of the perspective of FIG. 8.

As shown in FIGS. 8 and 9, each compartment 22, intended to receive a cartridge 1, comprises air-flow intake means 26 and exhaust means 27.

The intake means 26 are intended to be connected to the inlet 3 of the corresponding cartridge 1 and adapted to act on the corresponding means for shutting 5. In the present case, the intake means 26 associated with each compartment 22 comprise an intake circuit 30, an end of which is connected to first air-flow generation means 31. The other end of the intake circuit comprises a connection head 32 provided with an operating element 33 forming a finger adapted to push the shutter from the inlet of the cartridge 1.

According to the illustrated example, the first air-flow generation means 31 are formed by five air pulsers or fans, each affected to a compartment 22. The fans 31 are further controlled by the control unit U adapted to control the speed of rotation of the fans 31 and hence the flow rate thereof.

Figure 10:
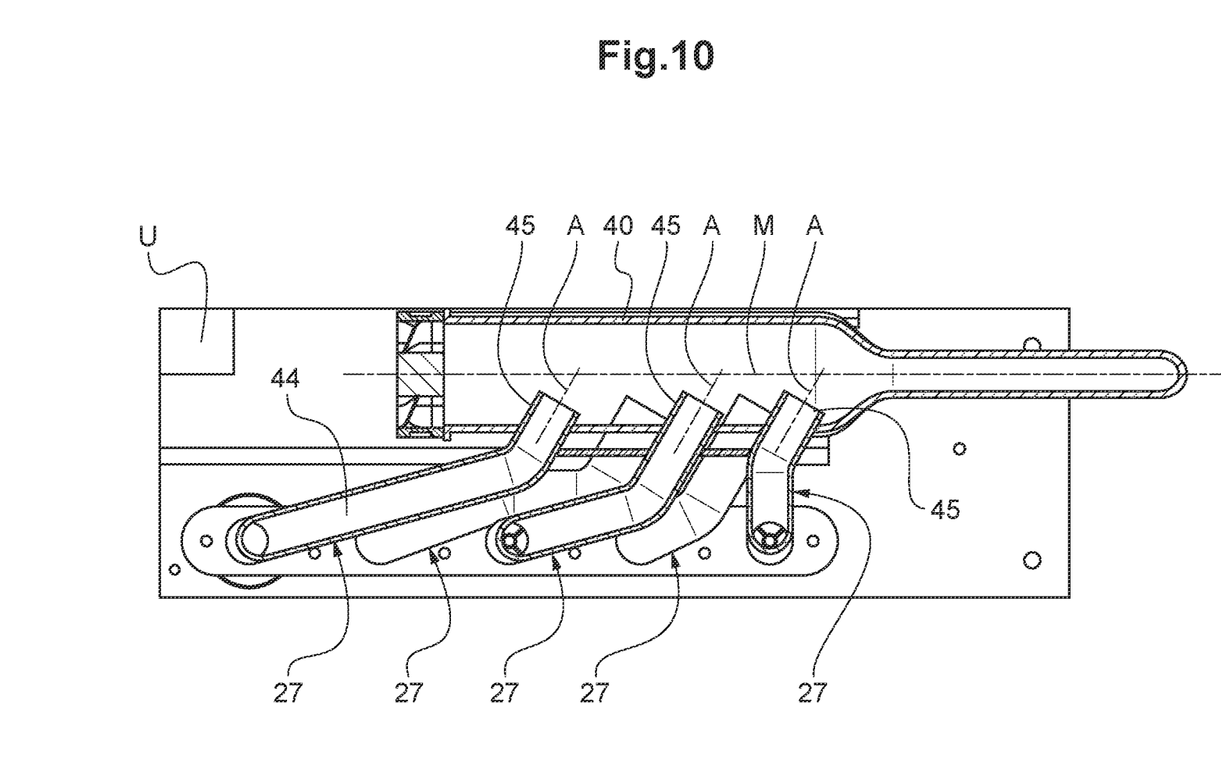
FIG. 10 is a cross-section along the plane XI-XI of FIG. 9.

The exhaust means 27 are intended to be connected to the outlet 4 of the corresponding cartridge 1 and adapted to act on the corresponding means for shutting 5 and are connected to a mixing chamber 40 as shown in FIG. 10.

In the illustrated example, the mixing chamber 40 has an elongated shape extending along a mean fibre M. The mixing chamber 40 is open to the outside at one of its ends, through a diffusion mouth 41, whereas its other end is connected to second air-flow generation means 42. In the present case, the flow generation means 42 are formed by an air pulser or fan piloted by the control unit U adapted to control the flow rate thereof.

The exhaust means 27 comprise, for each compartment 22, an exhaust circuit 44, an end of which is located at the compartment 22, by being substantially opposite the head 32 of the corresponding intake circuit 30. The end of the exhaust circuit 44 located at the compartment 22 has a connection head, not visible in the figures, similar to the head 32 of the intake circuit 30 and adapted, just as the latter, to act on the means for shutting 5 of the outlet 4 of a cartridge 1 located in the corresponding compartment 22 and to allow the opening thereof.

The other end 45 of the exhaust circuit 44 extends up to the mixing chamber 40 by protruding into the latter. It is to be noted that the section of the exhaust circuit 44 protruding into the mixing chamber 40 has a mean axis A that forms an acute angle lower than 90° with the mean fibre M of the mixing chamber 40. This arrangement limits the backflows in the exhaust circuit 34 and guarantees the quality of the mixture made in the chamber 40. Moreover, the extension in protrusion makes it possible to generate turbulences also favourable to the quality of the mixture. As a variant, other mixing means can be contemplated, for example a stirrer such as a blade with a rotary motion within the chamber or also a fixed blade acting as a deflector.

The fragrance diffuser according to the invention is implemented as follows.

Firstly, the drawer 23 of the device 20 is open to allow an access to the compartments 22. The user can then easily place a cartridge 1 into each compartment 22. The drawer 23 is then closed back so that the device is in stopped state, in a standby configuration, before being powered on. It is to be noted that, in this stopped state, all the cartridges placed in the compartments are closed by their means for shutting.

Then, the user powers on the diffuser by acting on an interface 60 of the control unit. According to the illustrated example, the interface is formed by a touch screen connected to the control unit. However, the interface can be made in any suitable way, such as, for example, in the form of an analog control or in the form of a radio interface, for example Wifi or Bluetooth, making it possible to interact with the control unit by means of a computer, a smartphone or a tablet/computer.

At the power-on of the diffusion device, the control unit performs the reading of the cartridge identification means in order to collect the data of these later and, in particular, the information relating to the odorant compositions contained in each of the cartridges.

The control unit then determines an operating mode on the basis of the identification of the cartridges and of pre-recorded programs, or based on instructions from the user, input on the interface. For the needs of the description, it will be considered that the operating mode retained aims to perform the diffusion of a fragrance composed of the mixture of the odorant compositions of all the cartridges present in the diffuser.

For that purpose, the control unit pilots the opening of the means for shutting of each of the cartridges. To that end, the control unit pilots actuators 61 that move the intake means 26 in translation, in the direction of arrow F1, towards the inside of the compartment, until the inlet of each cartridge is applied against the head 32 of the intake circuit and the outlet of each cartridge is applied against the head of the exhaust circuit 44. Hence, the fingers 33 push the corresponding means for shutting so that the inlets and outlets of the cartridges are open. It is to be noted that the application of the cartridges against the heads of the intake and exhaust circuits provides an airtight connection between the circuits and the cartridges. To that end, the heads may comprise sealing gaskets.

To provide the diffusion of the fragrance, the control unit U pilots the operation of the first and second air-flow generation means. Hence, the flows of air injected into the cartridges fill with odorant composition therein and mix together in the chamber 40. The modulation of the contribution of each of the odorant compositions to the final result is piloted by the control unit U that defines the speed of rotation of the fans assigned to each of the compartments and hence the air flow rate within these latter. Besides, the control unit U pilots the speed of rotation of the fan constituting the second air-flow generation means, which makes it possible in particular to modulate the residence time of the odorant composition in the mixing chamber.

It is to be noted that, when an odorant composition must not contribute to the fragrance diffused, the control unit U does not pilot the corresponding actuator 61 so as not to open said cartridge or, if the latter was in the open position, the control unit U pilots the operation of the actuator 61 is such a way as to displace the intake means in the direction of arrow F2. The cartridge is hence disengaged from the shutter operating means integrated to the intake and exhaust circuits. An automatic closing of said cartridge is hence provided.

Likewise, when the diffuser is not used, the control unit U pilots the actuators 61 in such a manner that all the cartridges are disengages and hence closed. It is to be noted that the control unit is adapted to allow a sequential diffusion of the odorant compositions of the cartridges, i.e. the use of the cartridges one after the other.

According to the illustrated example described hereinabove, the cartridge shutter operating means are passive. However, these operating means could be made in another manner and for example consisted of motorized fingers piloted by the control unit each acting on a shutter.

Figure 11:
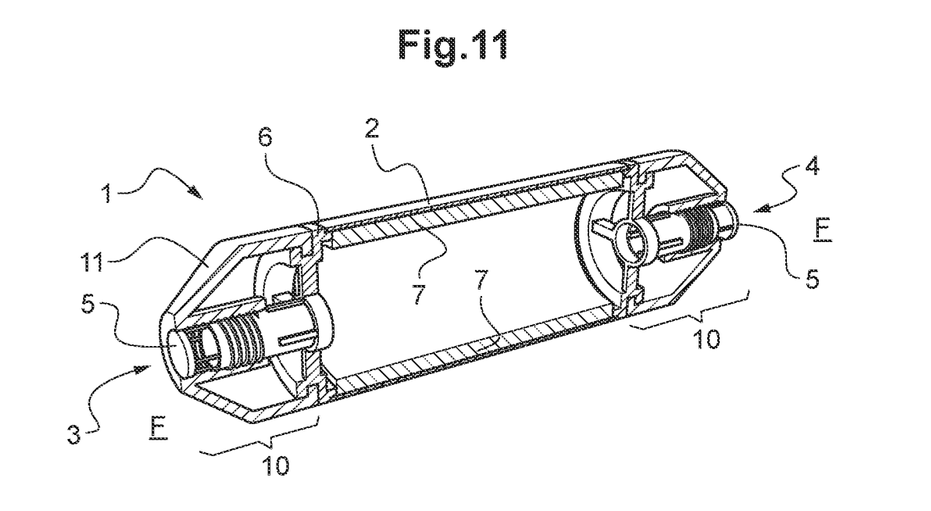
FIG. 11 is a view of a variant of a cartridge according to the invention, with the means for shutting in open position.
Figure 12:
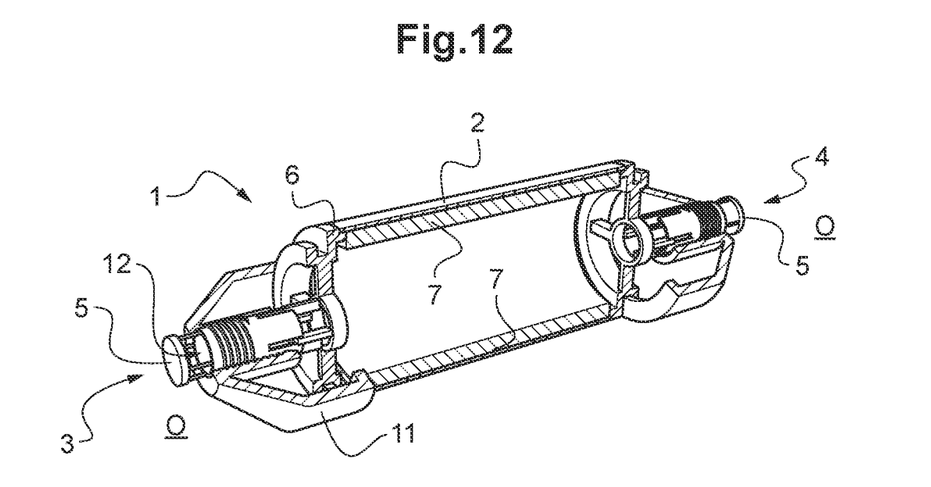
FIG. 12 is a view of the cartridge of FIG. 11 with the means for shutting in open position.
Figure 13:
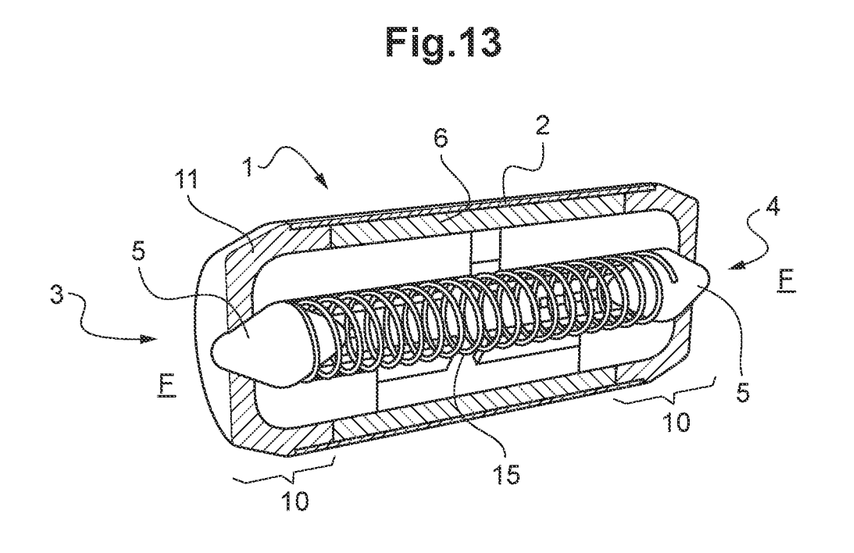
FIG. 13 is a view of another variant of a cartridge according to the invention, with the means for shutting of the latter in closed position.
Figure 14:
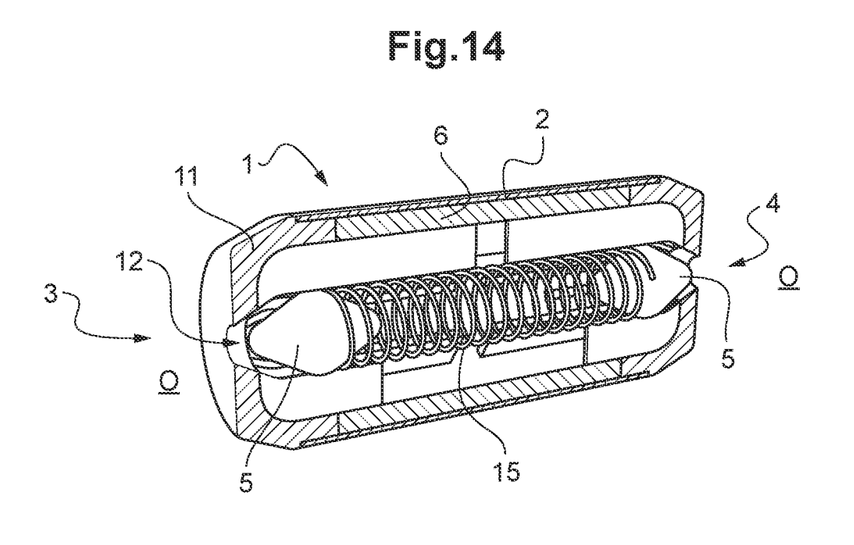
FIG. 14 is a view of the cartridge of FIG. 13, with the means for shutting in open position.

FIGS. 11 to 14 illustrate variant embodiments of the cartridge 1 according to the invention. These cartridges 1 are similar to the first version described. In FIG. 11, the body 2 of the cartridge comprises two plugs 10 that close the central portion 6 by immobilizing the accumulation means 7 inside the latter and that define the inlet 3 and the outlet 4, respectively, of the cartridge. Each plug 10 comprises a link element 11 airtightly fit on the central portion 6. The link element 11 further comprises a passage 12, visible in FIG. 12, forming the inlet 3 or the outlet 4 of the cartridge 1. The plug 10 further comprises a shutter 13 having the shape of a disk mobile in translation towards the outside of the cartridge. In FIG. 13, the shutters 13 have, at each end, a rounded elongated shape, and a single spring 15 pushes them against the opening so as to maintain the cartridge in the closed position F. Air-flow intake means 26 and exhaust means 27 come against the shutters 5 so as to place the cartridge in the open position, visible in FIG. 14.

Of course, various other variant embodiments of the cartridges, but also of the diffuser, may be contemplated within the framework of the appended claims.

The invention claimed is:

1. A fragrance dispensing device comprising a casing including:

at least two compartments, each adapted to removably receive a cartridge comprising an inlet and an outlet, an odorant composition, and means for shutting the inlet and the outlet of the cartridge, mobile between an open position and a closed position, each compartment comprising air flow intake means and exhaust means that are both intended to be connected to the inlet and the outlet, respectively, of a cartridge, and also adapted to act on the means for shutting the inlet and the outlet of the cartridge, so as to displace the means for shutting the inlet and the outlet of the cartridge to the open position, air-flow generation means, adapted to at least generate a flow of air passing through the compartments between the intake means and the exhaust means, a control unit adapted to control the air-flow generation means and the intake means and exhaust means and adapted to provide an independent, sequential or simultaneous diffusion, in variable proportions, of the odorant compositions contained in the cartridges and a closure of the cartridges when the apparatus is stopped.

2. The device according to claim 1, wherein the device comprises a mixing chamber that is open to the outside through a diffusion mouth and to which the exhaust means of each of the compartments are connected upstream from the diffusion mouth.

3. The device according to claim 2, wherein the mixing chamber has an elongate shape along a mean fibre, the diffusion mouth being at one end of the mixing chamber, and wherein the exhaust means are connected to the mixing chamber by pipes whose mean axis forms with the mean fibre of the mixing chamber an acute angle lower than 90 degrees, converging towards the diffusion mouth.

4. The device according to claim 3, wherein the connection pipes extend in protrusion inside the mixing chamber.

5. The device according to claim 1, wherein the air-flow generation means comprise first means connected to the intake means of the compartments.

6. The device according to claim 2, wherein the air-flow generation means comprise second means directly connected to the mixing chamber.

7. The device according to claim 6, wherein a second air-flow generation means are connected to the mixing chamber upstream from the connection of the exhaust means of the compartments to the mixing chamber.

8. The device according to claim 7, wherein the device comprises reading means intended to read identification means of the cartridges and the control unit is adapted to modify an operating mode of the device as a function of the readings.

9. The device according to claim 1, wherein at least one compartment has a shape complementary of that of a cartridge.

10. The device according to claim 2, wherein the air-flow generation means comprise first means connected to the intake means of the compartments.

11. The device according to claim 3, wherein the air-flow generation means comprise first means connected to the intake means of the compartments.

12. The device according to claim 4, wherein the air-flow generation means comprise first means connected to the intake means of the compartments.

13. The device according to claim 2, wherein the air-flow generation means comprise second means directly connected to the mixing chamber.

14. A cartridge comprising:
a hollow body provided with an inlet and an outlet,
means for accumulating at least one odorant composition, arranged in the hollow body, and
means for shutting the inlet and outlet, of the hollow body, the means for shutting being mobile between an open position and an airtight closed position,
means for biasing the means for shutting the inlet and outlet, in the airtight closed position.

15. The cartridge according to claim 14, wherein the means for shutting the inlet and the outlet of the cartridge comprise two shutters, one for the inlet and the other for the outlet.

16. The cartridge according to claim 14 wherein the means for shutting comprise at least one plug including:
a link element airtightly fit on the cartridge and comprising a seat defining a passage,
a shutter, mobile in translation, adapted to translate between an open position and a closed position of the passage
and the means for biasing the shutter in the closed position.

17. The cartridge according to claim 16, wherein the means for biasing comprise a spring.

18. The cartridge according to claim 14, wherein the cartridge has, at least locally, an external rotational asymmetry, so as to define a direction of introduction of the cartridge into a compartment intended to receive it.

19. The cartridge according to claim 14, wherein the means for accumulating at least one odorant composition comprise an absorbent material.

20. The cartridge according to claim 14, wherein the cartridge comprises an identification means suitable for an automatic reading.

* * * * *